United States Patent
Wuest et al.

[11] Patent Number: 5,559,219
[45] Date of Patent: Sep. 24, 1996

[54] MODIFIED PROCESS FOR THE DIRECT PRODUCTION OF ALKYL GLYCOSIDES

[75] Inventors: Willi Wuest, Ratingen; Joseph Wollmann, Herzogenrath; Rainer Eskuchen, Duesseldorf-Benrath, all of Germany

[73] Assignee: Henkel Kommanditgesellschaft auf Aktien, Duesseldorf, Germany

[21] Appl. No.: 952,535

[22] PCT Filed: May 31, 1991

[86] PCT No.: PCT/EP91/01010

§ 371 Date: Feb. 9, 1992

§ 102(e) Date: Feb. 9, 1992

[87] PCT Pub. No.: WO91/19722

PCT Pub. Date: Dec. 26, 1991

[30] Foreign Application Priority Data

Jun. 9, 1990 [DE] Germany .................. 40 18 583.4

[51] Int. Cl.$^6$ .................. C07H 1/00; C07H 3/02; C07H 15/04

[52] U.S. Cl. .................. 536/18.6; 536/18.5; 536/120; 536/124

[58] Field of Search .................. 536/18.6, 18.5, 536/120, 124

[56] References Cited

U.S. PATENT DOCUMENTS 5,043,091  8/1991  Joshi et al. .................. 252/174.17

FOREIGN PATENT DOCUMENTS

| 0096917 | 12/1983 | European Pat. Off. . |
|---|---|---|
| 0132046 | 1/1985 | European Pat. Off. . |
| 0362671 | 4/1990 | European Pat. Off. . |
| 9003977 | 4/1990 | WIPO . |

*Primary Examiner*—Michael G. Wityshyn
*Assistant Examiner*—Everett White
*Attorney, Agent, or Firm*—Wayne C. Jaeschke; John E. Drach; Henry E. Millson, Jr.

[57] ABSTRACT

Alkyl glycosides are produced by direct synthesis from higher monofunctional alcohols and powder-form glycoses, particularly anhydrous glucose and/or glucose monohydrate, in the presence of acidic catalysts at elevated temperatures, the interior of the reactor being kept under reduced pressure and the glycose being introduced with delay into the alcohol reactants present in excess therein, the alcohol reactants containing the acidic catalyst and being heated to the reaction temperature, while water released in the reaction mixture is removed from the reaction zone via the gas phase. A partial stream is run off from the liquid reaction mixture and delivered to a premixing zone into which the powder-form reactant is simultaneously introduced and is converted with the liquid partial stream into a paste which is delivered to the interior of the reactor via a following intensive mixer. The premixing zone is in direct pressure equalization with the reduced pressure of the reactor interior via the intensive mixer on the one hand and, at the same time, with the ambient pressure via the feed unit used for the powder-form glycose on the other hand, the consistency of the paste formed in the premixing zone being selected so that the paste serves as a pressure-equalizing sealing compound and, hence, as a so-called "living seal".

20 Claims, No Drawings

MODIFIED PROCESS FOR THE DIRECT PRODUCTION OF ALKYL GLYCOSIDES

BACKGROUND OF THE INVENTION

1. Field of the Invention

This invention relates to a further development of the production of surface-active alkyl glycosides by the so-called direct synthesis method. In this process, the alkyl glycosides, i.e. acetals of sugars and monofunctional alcohols, are prepared by direct acid-catalyzed reaction of the alcohols with the sugars with elimination of water.

2. Statement of Related Art

More particularly, the present invention relates to a further development of a process of the type mentioned which is described, for example, in International patent application WO90/03977 ("A Process for the Direct Production of Alkyl Glycosides"). In this document, the term alkyl glycosides is explained both in its broader form and, more particularly, in the narrower form used for practical purposes; those explanations also apply to the teaching of the present invention. The sugar components, hereinafter referred to as glycoses, comprise aldoses and also ketoses in the broadest sense. Aldoses are preferably used by virtue of their better reactivity. Glucose is particularly suitable by virtue of its ready accessibility and availability in industrial quantities, so that the invention is particularly concerned with the production of surface-active alkyl glucosides. The alkyl radical attached to the glucose by the acetal group is derived from monofunctional, preferably relatively long-chain alcohols, particular significance being attributed to corresponding alkyl radicals containing 8 to 20 carbon atoms. Particularly suitable alkyl radicals are derived from alcohols which have been obtained from natural materials, for example fats and/or oils of natural origin, although the invention is by no means limited to such alcohols. The term alkyl glycosides in this context encompasses compounds of the type mentioned in which the alkyl radicals are attached in acetal form to mononuclear and/or to polynuclear sugar residues.

Alkyl glycosides of the type mentioned, their production and their use, particularly as surface-active compounds, are the subject of numerous prior publications which are described in detail in applicants' above-cited earlier International application WO90/03977. This earlier international application also relates to a process for the direct production of alkyl glycosides by acetalization of higher aliphatic primary alcohols with glycoses, particularly glucose, in the presence of an acidic catalyst, rapid removal of the water of reaction, neutralization of the catalyst with a base, removal of the alcohol excess by distillation and conversion of the reaction product into an aqueous paste and bleaching of this paste, the aliphatic alcohol being used in an excess to the glycose and the formation and removal of the water of reaction taking place in vacuo and reaction temperatures above 80° C. being applied. The known process is essentially characterized in that a) mixtures of aliphatic primary alcohol, glycose and acidic catalyst are prepared and reacted at elevated temperature, either (i) part of the alcohol being initially introduced with the catalyst, the mixture being heated and a heated suspension of the glycose in the remaining quantity of alcohol being added continuously or in portions to the alcohol/catalyst mixture and the water of reaction formed being distilled off in vacuo, or (ii) a mixture of the entire alcohol and the glycose being initially introduced, heated and the acidic catalyst being added to the heated mixture, a vacuum subsequently being applied and the mixture being further heated until the reaction begins and the water of reaction being distilled off, b) the mixing ratios are selected so that the molar ratio of glycose to aliphatic alcohol is from 1:2 to 1:10 and preferably from 1:3 to 1:6, c) the reaction mixture is kept at that temperature and under that reduced pressure, preferably while mixing, until the water of reaction has been completely removed, d) the reaction mixture is subsequently cooled to approximately 90° C., after which an organic or inorganic basic alkali, alkaline-earth or aluminium or alkali/aluminium compound is added in such quantities that, over and above the neutralization of the acidic catalyst, a pH value of at least 8 and preferably in the range from 8 to 10 is adjusted and normal pressure is preferably only established thereafter, e) the excess alcohol is distilled off from the alkaline mixture in vacuo, preferably without preliminary filtration, to a value below 5% by weight of the reaction product by any of the methods known per se which do not damage the reaction product and f) the mixture is subsequently cooled to approximately 105° C. and a 30 to 60% paste is produced by addition of water and is stirred for about 0.1 to 5 hours at approximately 80° C. by the addition, preferably in portions, of active oxygen compounds, preferably hydrogen peroxide, measures optionally being taken by addition of alkali, preferably sodium hydroxide, to ensure that the pH value remains at 8 to 10 during this bleaching process. Preferred higher aliphatic primary alcohols for the production of the alkyl glycosides contain 8 to 20 carbon atoms and, more particularly, 12 to 18 carbon atoms.

The central reaction of the direct synthesis is the acid-catalyzed acetalization of the sugars used, more particularly glucose, with the monofunctional alcohols used in excess. To produce high-quality products on the one hand having the desired predetermined constitution and, on the other hand, the desired color and color stability, it has been found that the performance of this crucial step of the direct synthesis in practice is of very considerable importance. The above-cited International application WO90/03977 mentions several possibilities in this regard. The critical step a) of the process defined in the foregoing can be carried out in two ways, namely (a, i) and (a, ii). The first procedure referred to herein has the advantage that the water of reaction formed during the acetalization and/or the water introduced through the sugar reactants, for example glucose monohydrate, fed in can be rapidly and continuously removed from the reaction mixture. This is achieved by carrying out the acetalization under a low vacuum of, for example, about 10 to 50 mbar, so that the water of reaction can be removed via the vapor phase in view of the high reaction temperatures applied, namely above 100° C. and preferably of the order of 120° C. According to the earlier application, this continuous addition of the sugar reactants during the reaction is preferred. It is said to be best to select the addition rate so that a substantially clear phase is permanently present in the reactor, in other words the quantity of unreacted glycose in the reaction mixture is kept to a minimum. Another important aspect of this known process is that the mixture is preferably mixed and heated continuously during the reaction with only a slight temperature difference between the reactor wall and the reaction mixture, which is regarded as essential for avoiding overheating which would lead, for example, to unwanted deteriorations in the color of the reaction product. In the further description of this known process, it is stated how, for example, reaction temperatures of around 120° C. can be established in the reactor and maintained without reactor wall temperatures of more than about 125° C. having to be used.

DESCRIPTION OF THE INVENTION

The problem addressed by the present invention was to provide further improved conditions for the acetalization step, i.e. for the main reaction stage in which the sugars fed in are reacted with the monofunctional alcohols at high temperatures and greatly reduced pressures to form the alkyl glucoside.

Accordingly, the present invention relates to a process for the production of alkyl glycosides by direct synthesis from higher monofunctional alcohols and powder-form glycoses in the presence of acidic catalysts at elevated temperatures, the interior of the reactor being kept under reduced pressure and the glycose being introduced with delay into the alcohol reactants present in excess therein, the alcohol reactants containing the acidic catalyst and being heated to the reaction temperature, while water released in the reaction mixture is removed from the reaction zone via the gas phase. The new process is characterized in that a partial stream is run off from the hot liquid reaction mixture and delivered to a premixing zone into which the powder-form reactant is simultaneously introduced and is converted with the liquid partial stream into a paste which is delivered to the interior of the reactor via a following intensive mixer, the premixing zone being in direct pressure equalization with the reduced pressure of the reactor interior via the intensive mixer and, at the same time, with the ambient pressure via the feed unit used for the powder-form glycose, and in that the consistency of the paste formed in the premixing zone is selected so that the paste serves as a pressure-equalizing sealing compound.

According to the teaching of the invention, therefore, the alcohol reactant used in excess may be initially introduced as a whole into the reactor, heated therein to the reaction temperature and mixed with the acidic catalyst. In the process according to the invention, therefore, the glycose used in the form of a solid, more particularly in powder form, may be introduced into the reactor, preferably continuously, under constant reaction conditions in regard to temperature and vacuum, the rate at which the glycose is introduced being adaptable to the progress of the reaction which provides for optimal control both in regard to the contents of the reactor and, more particularly, in regard to the particular degree of conversion.

Accordingly, the technical solution to the problem addressed by the invention makes use of the feature of removing parts of the flowable phase initially introduced into or present in the reactor from the reactor under the process conditions and delivering them to a premixing zone into which the glycose reactant is simultaneously introduced in the form of a solid, preferably in powder form. In this premixing zone, a paste is formed from the circulated liquid phase and the solid phase introduced, the consistency of the paste being adjusted in such a way that it can act as a so-called "living seal". Despite the preferably continuous throughput of the Solid reactant to be introduced into the interior of the reactor kept under low pressure, the greatly reduced pressure prevailing in the interior of the reactor can be reliably adjusted. At the same time, it is possible carefully to control the course of the reaction inside the reactor and, hence, the consistency of the liquid phase present therein through the rate at which the paste is introduced into the interior of the reactor. After the introduction of the solid reactant in paste form has been completed, the reaction zone can be permanently closed by suitable mechanical elements, for example slides, so that the after-reaction phase can be carried out under pressures which, preferably, continue to decrease.

As in the state-of-the-art process cited above, internal reactor pressures below 100 mbar and preferably in the range from about 10 to 50 mbar during the glycose addition phase are applied in the process according to the invention. Accordingly, there is a considerable pressure difference between the interior of the reactor and the normal outside pressure which, typically, is just above 1,000 mbar. Accordingly, the paste functioning as a living sealing compound has to be adjusted in regard to its consistency in such a way that, in cooperation with the powder-form glycose introduced, for example, by a screw conveyor, it can act under the particular conditions prevailing as an actual sealing element against penetration of the far higher outside pressure into the interior of the reactor.

To prepare the paste, the liquid fed into the premixing zone is normally introduced under a slightly elevated pressure. The danger of this is that, if excessive liquid pressures are selected, parts of the liquid phase break through the powder-form glucose fed in from outside, preferably continuously. Accordingly, herein lies a second danger source for the uninterrupted and preferably continuous phase of the process in which the solid reactant is introduced under time control into the interior of the reactor.

In the preferred embodiment of the process according to the invention, disturbances of the type just mentioned are ruled out by applying reduced pressure in the premixing zone also. However, compared with the reduced pressure prevailing in the interior of the reactor, the reduced pressures adjusted in the premixing zone are lower and, in particular, are nearer the outside pressure than the greatly reduced internal pressure. The pressure in the premixing zone is preferably in the range from about 300 to 900 mbar, more particularly in the range from about 500 to 900 mbar, more preferably in the range from about 400 to 850 mbar and, most preferably, in the range from about 750 to 850 mbar. This pressure range is established by adapted control of the paste-forming liquid and solid material streams flowing into the premixing zone and by their preferably continuous discharge into the interior of the reactor. Selected mass ratios of the streams of liquid and solid reactants have proved to be of advantage for establishing the consistency of the paste acting as a living seal in the premixing zone. The preferred mass ratios of the liquid phase to the mass of the glycose reactant introduced is in the range from about 20 to 200:1.

In the International application cited at the beginning, it is pointed out that the fine dispersion of the glycose in the heated, catalyst-containing liquid alcohol reactant has a significant positive effect on the quality of the end reaction product. Accordingly, it is proposed to subject the mixture of active substances initially formed to fine dispersion by means of suitable, technical ultrafine mixing elements—and the teaching of the invention also makes use of this in its preferred embodiment. So-called inline mixers, for example of the stator/rotor type, have proved to be particularly suitable for this purpose. This fine dispersion has the desired side effect that the paste undergoes an increase in temperature during processing. More particularly, that unit of the reactor as a whole which is affected by the process according to the invention is designed, for example, as follows:

A premixing zone is provided separately from the main reaction, but in a direct pressure connection to the main reaction zone. The dry, preferably powder-form glycose reactant is delivered to this premixing zone, for example by a screw conveyor. At the same time, liquid phase is introduced into the premixing zone from the interior of the reactor through a branch pipe in accordance with the quantity of solid reactant introduced so that the paste acts as a living seal in the premixing zone, particularly in the range of the stated mass ratios of liquid phase to solid phase. From the premixing zone, the paste moves towards the interior of the reactor into the intensive mixer in accordance with the pressure gradient, i.e. for example into the following inline mixer from which it enters the interior of the reactor. Under these conditions, the rate at which the material passes through the premixing zone can be controlled virtually as required and optimally adapted to the course of the reaction in the interior of the reactor. The solid reactant may be added in batches and/or continuously, continuous delayed addition normally being preferred.

After the predetermined quantity of solid reactant has been added, the interior of the reactor is closed off from its surroundings. This may be done, for example, by means of a slide provided in the premixing zone which separates the premixing zone and the screw conveyor for the solid material from one another. During introduction of the glycose, the slide is opened. After the total quantity of solid reactant required has been added, the slide is closed. The acetalization reaction may then be continued in the interior of the reactor and may be terminated in the manner described in detail in the International application cited above. Following a suitable after-reaction time, the pressure of the plant may be further reduced, preferably to final pressures of a few mbar, for example to final pressures of 2 to 5 mbar. The reaction mixture is then slightly cooled, for example to temperatures of around 90° C., after which the catalyst is neutralized, basic pH values of at least pH 8 and, more particularly, in the range from pH 8 to 10 being adjusted, after which the excess alcohol is distilled off from the alkalized mixture in vacuo to small residual values by methods known per se which leave the reaction product intact. Finally, the crude reaction product is bleached in the manner already described.

Suitable acidic catalysts are, for example, sulfuric acid, phosphoric acid, sulfosuccinic acid, aliphatic and/or aliphatic-aromatic sulfonic acids containing 1 to 16 carbon atoms in the aliphatic part, for example p-toluene sulfonic acid and the like, which are typically used in quantities of from about 0.05 to 0.02 mol per mol of the glycose used. Preferred basic substances for neutralizing the acid catalyst and, in addition, for adjusting a basic pH value are inorganic, very finely powdered compounds from the group consisting of calcium hydroxide, calcium oxide, magnesium hydroxide, magnesium oxide, the zeolites NaA or NaX, preferably in combination with calcium hydroxide, and/or as organic compounds, the alcoholates of low-boiling alcohols preferably containing 1 to 4 carbon atoms in the form of their alkali metal and/or alkaline earth metal compounds. Particular significance is attributed to magnesium oxide and to the magnesium alcoholates, for example magnesium ethylate. Half to three quarters of the equivalent quantities of these basic magnesium compounds may even be replaced by alkali hydroxide or carbonate, more particularly NaOH (i.e. 2 mol basic Na compounds per 1 mol basic Mg compound) for neutralization of the catalyst and, in addition, adjustment of a basic pH value in the range from pH 8 to 10. The excess alcohol is distilled off in a vacuum which allows sump temperatures of 160° to 170° C., removal of the excess alcohol by distillation in short-path evaporators being particularly suitable. Falling-film evaporators or thin-layer evaporators are particularly suitable for industrial batches.

The reaction products of the invention are mixtures of alkyl monoglycoside and the oligomerization products having a degree of oligomerization of up to about 5. The average degree of oligomerization is preferably at most about 1.5 and more particularly from 1.2 to 1.4. The reaction is controlled in particular in such a way that the quantity of alkyl monoglucoside, based on the total quantity of alkyl monoglucoside and alkyl oligoglucoside, is distinctly above 70% by weight. To this end, molar ratios of glycose to higher alcohol of 1:2 to 1:10 and more particularly 1:3 to 1:6 are preferably applied. The quantities of residual alcohol, based on anhydrous product, should be at most about 5% by weight and, more particularly, are in the range from about 0.5 to 2.5% by weight. Aqueous pastes containing 30 to 60% by weight water can be formed from the reaction products. These pastes also contain the salts emanating from the neutralization of the catalyst and the bleaching step. The stability of the alkyl glycosides in storage can be improved by addition of antimicrobial agents in small quantities.

EXAMPLE

To prepare a washing-active alkyl glucoside compound, the following reactants were reacted in a stirred reaction vessel (2.5 m$^3$): 1,213 kg C$_{12-14}$ fatty alcohol (Lorol Spezial, a product of Henkel KGaA), 250 kg anhydrous glucose and—in a parallel test—275 kg glucose monohydrate, 1.1 kg sulfosuccinic acid as catalyst, 1.3 kg magnesium ethylate as neutralizing agent.

The plant used for the reaction was constructed as follows:

Parts of the liquid contents of the reactor could be removed through a valve installed in the bottom of the reaction container and a circulation pipe and reintroduced at the head of the reaction vessel. The liquid transport was provided with a pump arranged in the circuit. The circulation pipe was heated. The partial stream of liquid removed was fed to a mixing element which was arranged outside the reaction vessel and which was connected by an intensive mixer (inline mixer) to the interior of the reaction vessel while, at the same time, the powder-form glucose reactant could be introduced into the mixing element by means of a screw conveyor. The procedure adopted was as follows:

The total quantity of fatty alcohol and the catalyst were introduced into the reactor and heated to the reaction temperature of 110° to 120° C. with simultaneous circulation via the circulation system. The plant pressure was reduced to 10 to 20 mbar. During this startup phase, the screw conveyor for the powder-form glucose was separated from the system by means of a closed slide.

After the above-stated values for the reaction temperature and the set pressure had been reached, introduction of the glucose was started by switching on the inline mixer and the screw motor and by opening the flat slide. For a recirculation volume of 10 m$^3$/h of the liquid contents of the reactor, 250 kg anhydrous glucose were introduced via the mixer over a period of about 40 minutes in a first test while 275 kg glucose monohydrate were introduced over a period of 75 minutes in a second parallel test. The vapors (distillates) issuing from the reactor were freed from entrained fatty alcohol in a first condenser (warm water at 25° C.), the water of reaction being deposited in a second condenser.

In both cases, addition of the glucose was followed by an after-reaction time of 1.5 h during which the plant pressure was reduced to approx. 2 to 3 mbar using a two-stage steam-jet pump.

Neutralization was carried out in vacuo with magnesium ethylate. After a pH value above 8 had been adjusted, the reaction mixture was transferred to an intermediate storage tank. The excess fatty alcohol was then removed by distillation. The alkyl glycoside compound obtained was bleached in known manner, for example with hydrogen peroxide.

What is claimed is:

1. A process for the production of alkyl glycosides comprising the steps of
   A) heating a mixture of an alcohol and an acidic catalyst in a reaction zone;
   B) circulating a portion of said mixture to a premixing zone maintained at a pressure in the range of from about 300 to about 900 mbar and mixing said mixture with a solid glycose to form a paste;
   C) introducing said paste into the reaction zone which is maintained at a pressure below 100 mbar; and
   D) continuing the reaction in the reaction zone to produce the alkyl glycoside product;

wherein the alcohol in step A) is the total quantity of alcohol used in the process.

2. The process of claim 1 wherein the pressure in said premixing zone is in the range of from about 500 mbar to about 900 mbar.

3. The process of claim 2 wherein said pressure range is from about 400 mbar to about 850 mbar.

4. The process of claim 1 wherein the mass ratio of liquid phase to glycose is from about 20:1 to about 200:1.

5. The process of claim 1 wherein said glycose is anhydrous glucose or glucose monohydrate.

6. The process of claim 5 wherein the pressure in step D) is in the range of from about 2 mbar to about 5 mbar.

7. The process of claim 1 wherein the molar ratio of glycose to alcohol is from about 1:2 to about 1:10.

8. The process of claim 7 wherein said molar ratio is from about 1:3 to about 1:6.

9. The process of claim 1 wherein said alcohol is a $C_{8-20}$ fatty alcohol.

10. The process of claim 9 wherein said alcohol is a $C_{12-18}$ fatty alcohol.

11. The process of claim 1 wherein in step B) the solid glycose is in the form of a powder.

12. The process of claim 1 wherein steps B) and C) are carried out continuously until all of the solid glycose has been introduced into the reaction zone in the form of a paste.

13. The process of claim 1 wherein in step c) the pressure in the reaction zone is maintained in the range of from about 10 to about 50 mbar.

14. The process of claim 1 wherein step A) is carried out at a temperature in the range of from about 110 to about 120° C.

15. The process of claim 1 wherein in step B) the paste has a consistency such that in step C) the paste acts as a sealing agent to maintain the low pressure in the reaction zone.

16. The process of claim 1 wherein water of reaction is removed from the reaction zone in gaseous form.

17. The process of claim 1 wherein following step D) the acidic catalyst is neutralized and excess alcohol is distilled off.

18. The process of claim 1 wherein in step B) said mixture and the solid glycose are simultaneously introduced into the premixing zone.

19. The process of claim 1 wherein the mass ratio of liquid phase to glycose is from about 20:1 to about 200:1; the alcohol in step A) is a $C_{8-20}$ fatty alcohol; in step B) the solid glycose is in the form of a powder, the pressure in the premixing zone is in the range of from about 500 mbar to about 900 mbar, and the paste has a consistency such that in step C) the paste acts as a sealing agent to maintain the low pressure in the reaction zone; steps B) and C) are carried out continuously until all of the solid glycose has been introduced into the reaction zone in the form of a paste; and in step c) the pressure in the reaction zone is maintained in the range of from about 10 to about 50 mbar.

20. The process of claim 19 wherein said glycose is anhydrous glucose or glucose monohydrate.

* * * * *